US009606032B2

(12) United States Patent
Gooley et al.

(10) Patent No.: US 9,606,032 B2
(45) Date of Patent: Mar. 28, 2017

(54) PREPARATION OF SAMPLES FOR ANALYSIS AND SAMPLING DEVICE THEREFOR

(71) Applicant: Trajan Scientific Australia Pty Ltd, Ringwood, Victoria (AU)

(72) Inventors: Andrew Gooley, Ringwood (AU); Hans-Jurgen Wirth, Ringwood (AU); Emily Frances Hilder, Sandy Bay (AU); Wei Boon Hon, Sandy Bay (AU)

(73) Assignee: Trajan Scientific Australia Pty Ltd, Ringwood, Victoria (AU)

( * ) Notice: Subject to any disclaimer, the term of this patent is extended or adjusted under 35 U.S.C. 154(b) by 0 days.

(21) Appl. No.: 15/178,485

(22) Filed: Jun. 9, 2016

(65) Prior Publication Data

US 2016/0290902 A1    Oct. 6, 2016

Related U.S. Application Data

(62) Division of application No. 14/608,061, filed on Jan. 28, 2015, now abandoned.

(30) Foreign Application Priority Data

Jan. 29, 2014    (AU) ................................ 2014900265

(51) Int. Cl.
*B01L 9/00*    (2006.01)
*G01N 1/40*    (2006.01)
*G01N 1/10*    (2006.01)
*B01L 3/02*    (2006.01)

(52) U.S. Cl.
CPC ............ *G01N 1/405* (2013.01); *B01L 3/0275* (2013.01); *G01N 1/10* (2013.01); *B01L 2200/0631* (2013.01)

(58) Field of Classification Search
CPC .................................. G01N 1/405; B01L 9/00
See application file for complete search history.

(56) References Cited

U.S. PATENT DOCUMENTS

2002/0103538 A1*    8/2002    Hughes .................. A61L 15/24
623/6.59
2005/0101025 A1*    5/2005    Ho ........................ B01L 3/0275
436/86

FOREIGN PATENT DOCUMENTS

JP              2005345379        * 12/2005

* cited by examiner

*Primary Examiner* — Jyoti Nagpaul
(74) *Attorney, Agent, or Firm* — Fulwider Patton LLP

(57) ABSTRACT

A sampling device comprising a body that defines a fluid flow path from an inlet opening, wherein the flow path includes a bed of a porous polymer monolith selected to adsorb bioparticles from a matrix drawn or dispensed through the inlet opening and the bed.

9 Claims, 6 Drawing Sheets

C* - centrifugation and T* - plasma sampling device

Figure. SEM images of plasma sampling polymer with RBC

PREPARATION OF SAMPLES FOR ANALYSIS AND SAMPLING DEVICE THEREFOR

CROSS-REFERENCES TO RELATED APPLICATIONS

This divisional application is based upon U.S. Ser. No. 14/608,061, filed on Jan. 28, 2015, which claims priority from Australian Application No. 2014900265, filed Jan. 29, 2014, which are incorporated by reference in their entirety herein.

FIELD OF THE INVENTION

This invention relates generally to the sampling and preparation for analysis of matrices containing bioparticles. The invention is concerned, in one aspect, with a method for preparing such matrices for analysis, and in another with a sampling device. The sampling device may typically be a pipette tip or other tubular embodiment such as a polypropylene cartridge typically used for solid phase extraction (SPE), a microwell plate or a polymer needle. Matrices of particular interest include whole or undiluted blood, plasma, tissue culture fluids and other matrices with suspended bioparticles.

BACKGROUND

The separation of cells from their extracellular matrix (ECM) is commonly achieved through centrifugation. Typically, the cells are pelleted and the extracellular supernatant is aspirated following the centrifuging step.

There is an increasing interest in microsampling, i.e. sample volumes of the order of 1.0 to 100 µL. By way of example, it is straightforward to extract a small volume of human whole blood into a capillary device such as a pipette tip following a finger prick with a sterile blood lancet. Typically 50 to 80 µL in volume is collected. In the context of bioparticles in general or cells in particular, such small volumes are not easy to centrifuge and so the traditional methods of sample preparation using centrifugation become problematical. Moreover, there is an interest in microsampling strategies where the sample can be processed using automated pipetting platforms such as the Tecan Genesis 200 or strategies remote from an actual laboratory environment, where centrifuges may not be readily available. A simple example of such a context is the analysis of blood samples collected by skin pricking, e.g. from a finger, in humans. Thus, sample collection and preparation can often be a bottleneck in the process of developing a robust and reliable point-of-care device from microsampling and testing.

It is an object of the present invention to at least in part address the limitations of sample preparation techniques based on centrifugation, and to thereby provide improvements suitable for use in microsampling techniques.

SUMMARY OF THE INVENTION

International patent publications WO 2011/082449 and WO 2013/006904 disclosed the use of porous polymer matrix or porous polymer monolith materials as media for the storage of biological fluids, including body fluids such as whole blood or blood plasma. As described therein, porous polymer monoliths are highly cross-linked structures that can function as a stationary support and consist of a fused array of microgobules separated by pores. Polymer monoliths can be fabricated from a mixture containing a cross-linking initiator and monomers dissolved in pore-forming solvents known as porogens or porogenic solvents. In embodiments of particular interest, such porous polymer monoliths can be formed from one or more acrylic acid mononers, especially methacrylates.

The present invention entails an appreciation that porous polymer monoliths can usefully be employed in a device for microsampling by solid phase extraction (SPE). It has been found that when a matrix containing bioparticles is drawn or dispensed through a body or plug of porous polymer monolith, the porous polymer monolith adsorbs bioparticles, allowing extraction of the extracellular matrix. By employing a functionalised monomer and a selected combination of alcohols and alkanes as porogenic solvents, the device can be optimised to substantially wholly retain the bioparticles in the porous polymer monolith, enabling aspiration and/or dispensing of the matrix fraction.

According to one aspect of the invention, there is provided a sampling device comprising a body that defines a fluid flow path from an inlet opening, wherein the flow path includes a bed of a porous polymer monolith selected to adsorb bioparticles from a matrix drawn or dispensed through the inlet opening and the bed.

In a further aspect, the invention provides a method of preparing for analysis a matrix containing bioparticles, comprising:

drawing or dispensing a volume of the matrix along a flow path defined by a sampling body through a bed of porous polymer monolith in the flow path, which bed is of sufficient length along the flow path whereby the bed adsorbs the bioparticles and a sub-volume of the matrix substantially free of the bioparticles remains adjacent to the bioparticles in the sampling body; and recovering matrix from the sub-volume for analysis.

The porous polymer monolith may be porous polymer monolith as disclosed in international patent publication WO 2011/082449 or international patent publication WO 2013/006904, the whole contents of which documents are herein incorporated by reference. The porous polymer monolith may be a result of polymerisation of one or more monomers in the presence of two or more porogens. Of particular interest is a porous polymer monolith formed from one or more functionalised monomers, including a hydrophilic monomer, in the presence of a cross-linking initiator and a selected ratio of porogenic solvents. A suitable hydrophilic monomer is 2-hydroxyethylmethacrylate (HEMA) and the porogenic solvents, or porogens, may typically be a mixture of one or more alcohols and one or more alkanes.

The monomers may be methacrylates and may further include ethylene dimethacrylate (EDMA). A useful mixture of alcohols and alkanes may include methanol, dodecanol, n-hexane and cyclohexanol.

Advantageously, the porous monomer monolith is fabricated in situ in the tubular body by electromagnetic radiation, e.g. ultraviolet, initiation. For this purpose, the cross-linking initiator is an appropriate radiation responsive initiator known to those skilled in the art. A suitable reagent for ultraviolet initiation is 2,2-dimethoxy-2-phenylacetone (DMPA).

Advantageously, the body is a tubular body. Preferably, the bed is a plug of the porous polymer monolith that fills a cross-section of the flow path. The sampling device may be a pipette tip. In other embodiments, the sampling device may be a polypropylene cartridge adapted for SPE, a microwell plate or a polymer needle.

In advantageous adaptation of the method of the invention, there is a further step of adsorbing the sub-volume of the matrix onto a second device such as an immobilised enzyme reactor.

In a particular useful application of the invention, the matrix containing bioparticles is whole blood and the matrix itself is the blood plasma fraction. Depending on the speed of the spin the plasma can be platelet-free.

In an embodiment, the porous polymer monolith may be selected to adsorb at least red blood cells from whole or buffered blood. In another embodiment, the porous polymer monolith may be selected to additionally adsorb white blood cells and platelets from the whole or buffered blood whereby to obtain a cell-free plasma or plasma-like fraction.

BRIEF DESCRIPTION OF THE DRAWINGS

The invention will now be further described by way of example only, with reference to the accompanying drawings, in which.

DETAILED DESCRIPTION OF THE PREFERRED EMBODIMENTS

Figure 1:
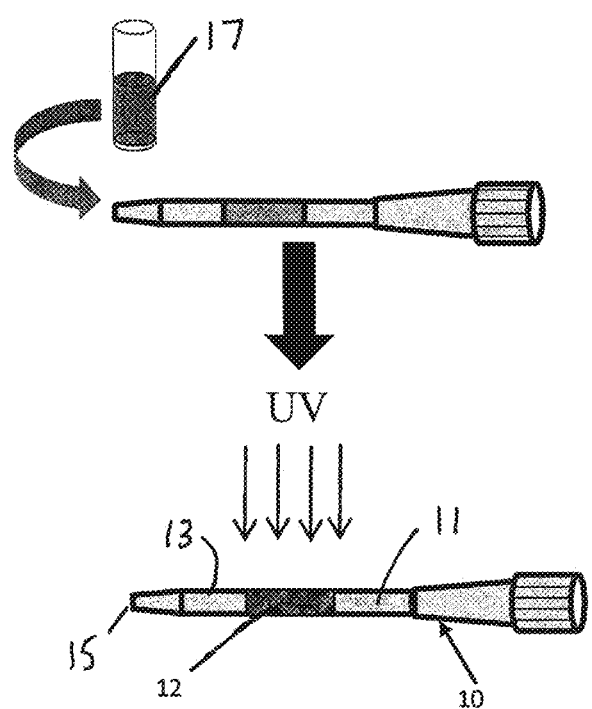
FIG. 1 is a schematic diagram depicting a sampling device according to an embodiment of the invention, and also showing the making of the device by in situ preparation of a porous polymer monolith bed in a polypropylene pipette tips.
Figure 2:
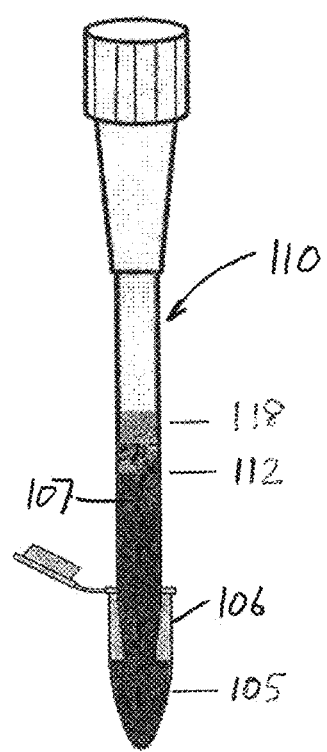
FIG. 2 depicts blood plasma separation employing the modified pipette tip of FIG. 1 containing a bed of a porous polymer monolith.

FIGS. 1 and 2 illustrate an embodiment of sampling device according to the invention, more specifically a tubular sampling device in the form of a pipette tip 10 modified to incorporate within its central passage 11 a bed 12 of porous monomer monolith. Bed 12 is a plug that fills a cross-section of passage 11. The passage forms a flow path defined by the body 13 of the pipette tip 10, extending from the inlet opening 15. The porous polymer monolith is a result of polymerisation of one or more monomers in the presence of two or more porogens. The pipette tip is any known or commercial pipette tip but may of course be specially fabricated or adapted for use in the present invention.

In accordance with a preferred procedure for making the sampling device, the bed of porous polymer monolith is fabricated in situ, i.e. cast in place, employing ultraviolet initiation. The pipette tip is polypropylene. The polymer monolith is methacrylate-based and has hydrophilic functionality. More specifically in this case, the monomers are HEMA and EDMA, the cross linking initiator is DMPA 1 wt % with respect to the amount of monomer, and the porogenic solvents are methanol, 1-dodecanol, n-hexane and cyclohexanol. With this collection of reagents forming polymerization mixture 17, the required irradiation time is about 5 minutes.

It will be understood that this fabrication technique and the resultant sampling device is merely exemplary. Other polymerisation mixtures will be known to those skilled in the art, as will be modified or alternative initiation processes.

A number of sampling devices comprising modified pipette tips were made by the above method. The thus formed pipette tips were variously used as a porous sampling device to separate red blood cells from whole blood. This is illustrated in FIG. 2.

For a given application, the bed or plug 12 of the sampling device is of sufficient length along the flow path whereby the bed adsorbs the bioparticles of a matrix drawn or dispensed through the bed, and a sub-volume of the matrix substantially free of the bioparticles remains adjacent to the bioparticles in the sampling body.

With reference to FIG. 2, the whole blood was diluted 1:1 with cold isotonic buffer and the resultant 50% blood solution 105 was aspirated from a receptacle 106 through a pipette tip 110 containing the bed 112 of porous polymer monolith (PPM) as described above, of a bed volume of approximately 25 µL. Aspiration was monitored until the red blood cell (RBC) fraction 107 appeared within 0.5 to 1.0 mm of the top of the PPM bed 112. The clear "plasma-like" fraction or sub-volume 118 above the bed was recovered using a gel loader pipette tip for analysis. This fraction or sub-volume could in other cases be recovered by aspirating or dispensing the fraction.

Evidence that the RBC fraction was being adsorbed to the porous polymer monolith as an SPE bed, and not simply filtered, was demonstrated by repeating the experiment with a bed in which the hydrophilic monomer HEMA was substituted by the hydrophobic monomer butyl methacrylate (BMA). In this case, the RBC fraction was not retained and went straight through the bed. This result strongly indicates that the device of the invention is adsorbing the RBC fraction rather than filtering the red blood cells, as is a common approach in prior sampling techniques.

Figure 3:
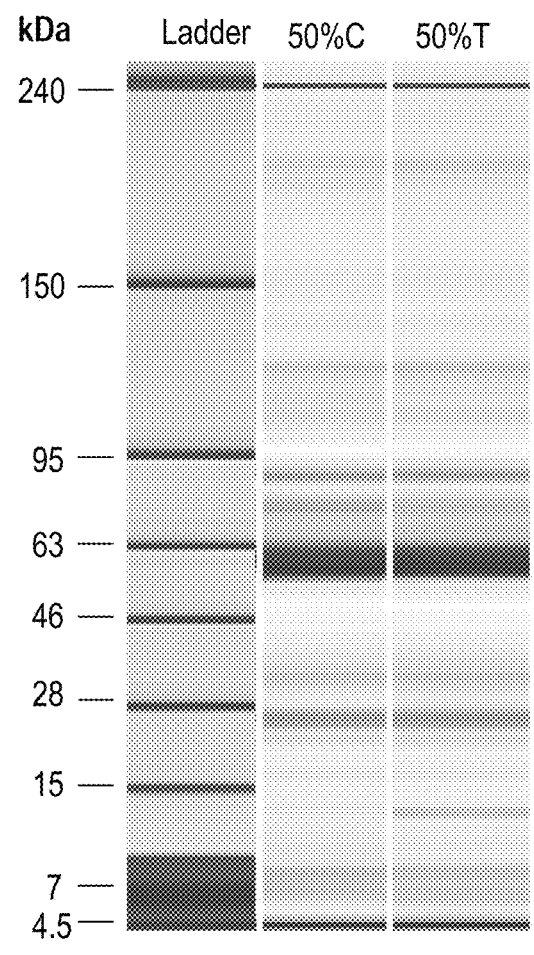
FIG. 3 is a gel image of plasma obtained from 50% blood solution, respectively for centrifuged plasma and for plasma obtained using the sampling device of FIG. 1.

The clear plasma-like fraction was analysed by SDS-PAGE to determine whether there were any gross differences between the fraction obtained with the device according to the invention and a corresponding fraction obtained by centrifugation. The resultant gel image shown in FIG. 3 indicates that at this level of analysis the fractions were fundamentally the same. The fraction from the sampling device (right hand column) looks very similar to the centrifuged sample (centre column), albeit a slightly darker band is evident near 15 kDa in the sampling device column, which is haemoglobin (indicative of either a little lysis or a few RBC).

The morphology of the red blood cells on the porous polymer monolith was examined by scanning electron microscopy. In order to take cross-sectional SEM images of the pipette tips with blood cells, samples approximately 3 mm in length were cut from the tip with a razor blade after separation. The tip sections were gently washed with phosphate buffered saline (PBS) and fixed in 2.5% (v/v) glutaraldehyde in PBS for 2 hr at 4° C. Then, the samples were slowly dehydrated by successive immersions in aqueous solutions of 30, 75, 90, 95, 100, and 100% (v/v) ethanol and critical point dried in Blazers Critical Point Drier CPD 030 (Bal-Tec Inc, Blazers, Liechtenstein). Samples were sputter-coated with a thin layer of platinum using an EIKO IB5 high-resolution platinum coater. Subsequently, the samples and morphologies of the blood cells were examined by scanning electron microscopy (SEM) using a FEI Quanta 600 MLA ESEM.

Figure 4:
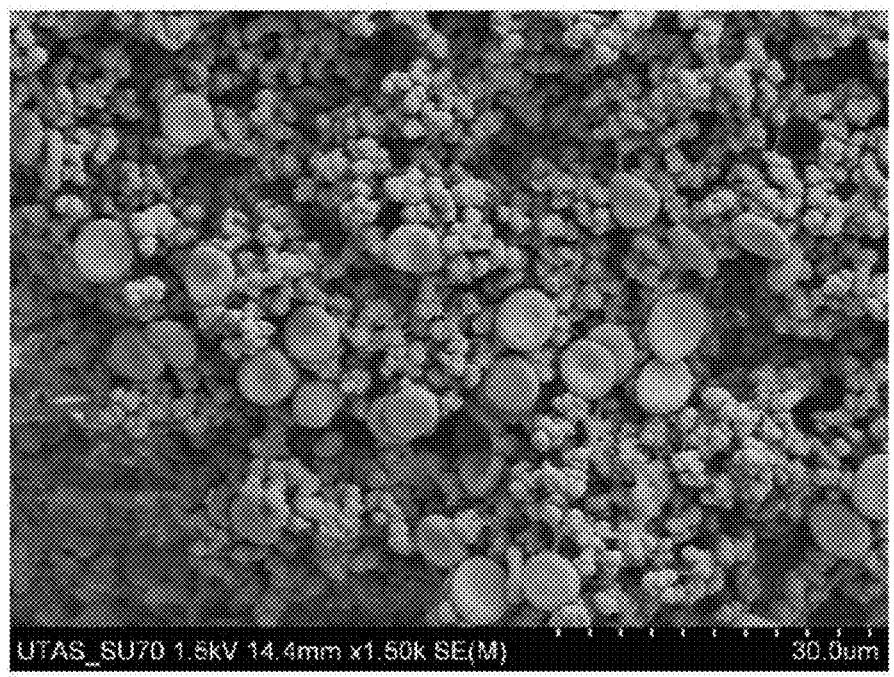
FIG. 4 is an SEM image of a section of the porous polymer monolith of a sampling device after use with whole blood, depicting the distribution of red blood cells adsorbed therein.

A sample SEM image is provided in FIG. 4. This shows a good distribution of intact red blood cells across the visible section of the porous polymer monolith. Distribution rather than clumping demonstrates that the red blood cells have been adsorbed rather than filtered. Distributed adsorption entails a lowered risk of lysis, resulting in contamination of the extracellular matrix, i.e. the "plasma-like fraction", with hemoglobin. Preventing such contamination is highly desirable in order to optimise subsequent analytical testing of the plasma-like fraction.

In order to test how the sampling device of FIG. 1 efficiently removes the bioparticles, the numbers of RBCs, white blood cells (WBCs) and platelets in an initial whole blood sample and in the collected clear plasma-like fraction were counted with a haemocytometer ((Bürker, Labor Optik, UK). For RBC count, the blood sample or plasma-like fraction was diluted by 1:200 or 1:100 using Gower's solution (5.25% sodium sulfate and 16.65% acetic acid in water). For WBC count, the blood sample or plasma-like fraction was diluted by 1:20 or 1:10 using WBC diluting fluid (2% glacial acetic acid and 4% of 0.5% crystal violet solution in water). To determine the platelets number, the blood sample or plasma-like fraction was diluted by 1:100 or 1:50 using 1% ammonium oxalate solution. All the solutions were mixed gently and allowed to sit for 5 min before counting using a haemocytometer under a Leica microscope (Leica microscope (Leica DMLM, Weizlar, Germany). The platelets and RBCs were counted using 40× objective with reduced condenser aperture. The WBCs were counted with a 20× microscope objective. The bioparticles removal efficiency of the sampling device was found to be 100%, 98% and 97% for RBCs, WBCs and platelets.

Other exemplary applications of the inventive sample device and method include to miniaturise cell culture experiments, where cells grown in microtitre plates are rapidly processed to harvest the cell supernatant from the cells in very small culture volumes.

Figure 5:
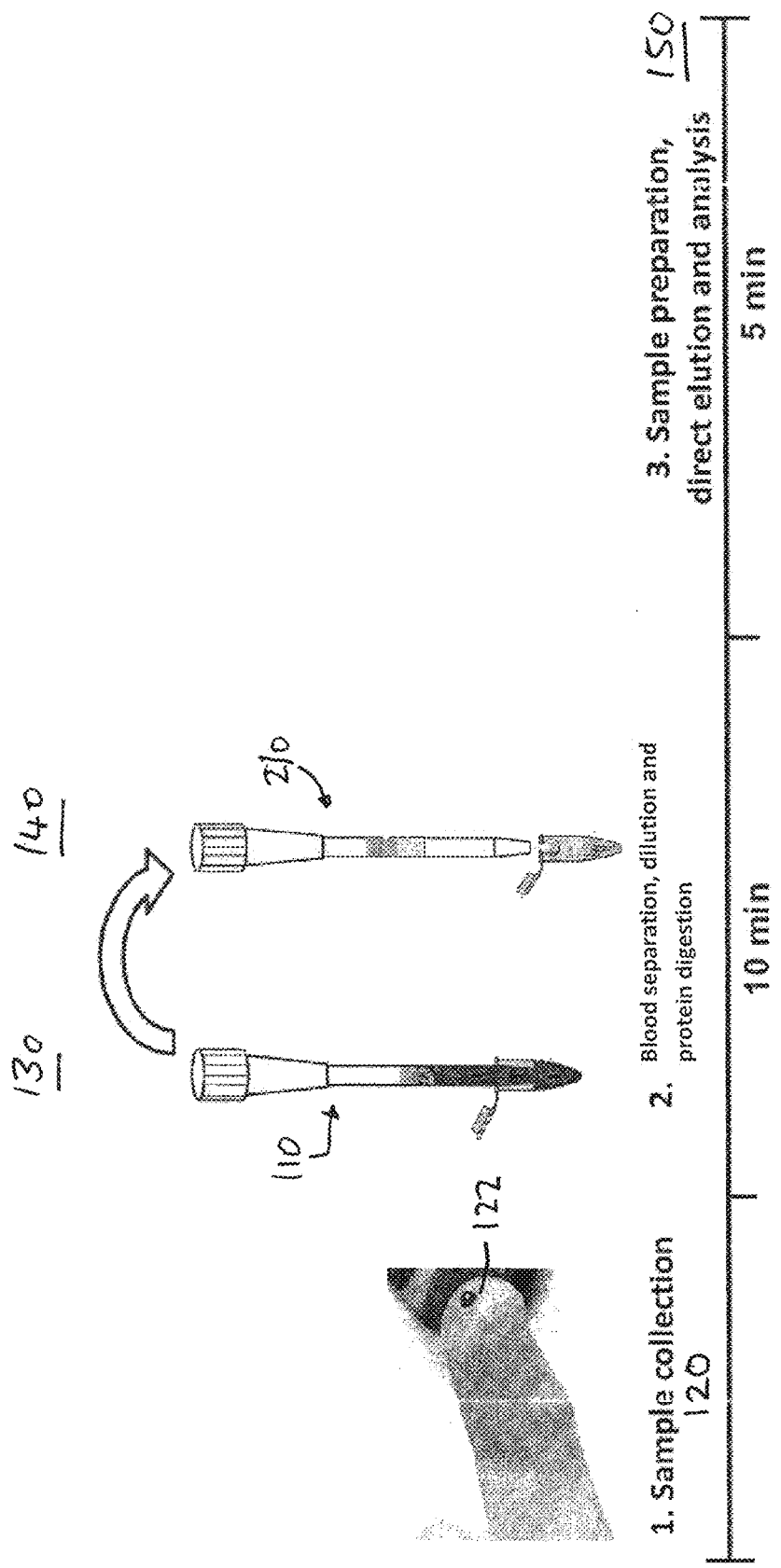
FIG. 5 diagrammatically depicts a sampling workflow scheme employing a sampling device according to an embodiment of the invention.

An important advantage of the invention is the potential for a simplified more expeditious sample preparation workflow. By way of example, a traditional sample preparation for whole blood involves the extraction of a sample by venous puncture from a patient's arm, blood centrifugation and dilution (20 to 30 minutes), a sample preparation step including in-solution digestion and peptide enrichment (greater than 12 hours) and a final analysis and data processing step (greater than 2 hours). In a microsampling technique utilising the concepts of the invention, depicted schematically in FIG. 5, sample collection 120 is by blood droplet from a finger prick 122. Two separate sampling devices 110, 210 according to the invention are employed for plasma/RBC separation 130 and protein digestion 140 (about 10 minutes), followed by a sample preparation, direct elution and analysis step 150 (5 minutes). By way of example, a "surrogate" protein cytochrome C, was spiked into whole blood and unique parent ions (ions generated in a mass spectrometer) were identified at a sensitivity of 300 fmol following processing using the combination of SPE devices described above in less than 30 minutes.

An emphasis herein has been the recovery of a cell-free fraction, e.g. a cell-free plasma-like fraction from blood. It will be appreciated that, conversely, the invention also provides a mechanism for recovering a cell-rich fraction.

Figure 6:
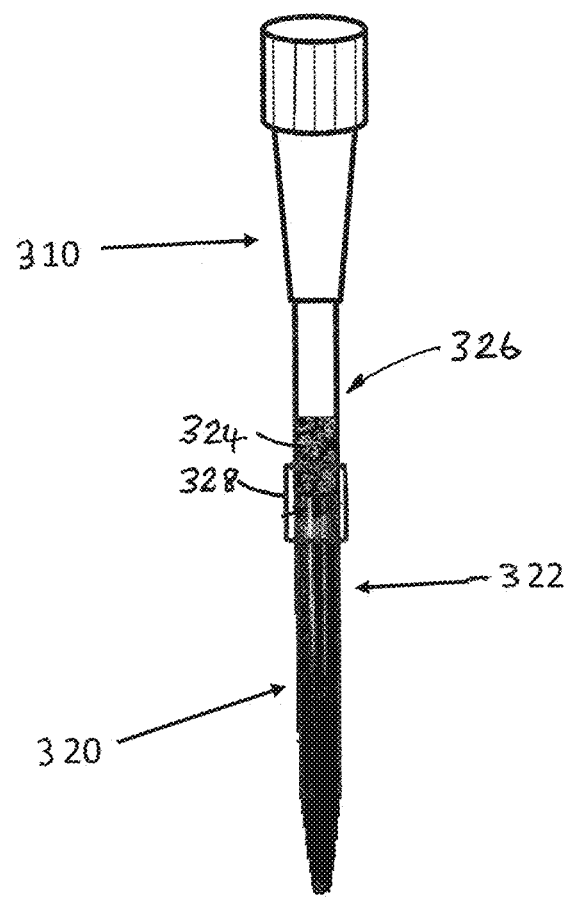
FIG. 6 is a diagram of a two-component device incorporating a porous polymer monolith bed.

In another embodiment, schematically depicted in FIG. 6, the sampling device 310 may comprise a separable multi component device in which the porous polymer monolith is contained in a chamber of a first component 320 and the structure is such that when the matrix is drawn or dispensed through the porous polymer monolith bed 322, the sub-volume 324 of the matrix substantially free of the bioparticles is substantially contained in a chamber of a second component 326 serving, in this case, as an immobilised enzyme reactor SPE device. Components 320, 326 are joined by a silicone septum 328. With this arrangement, the sub-volume of the matrix can be recovered by thereafter separating the components at the septum.

The invention claimed is:

1. A method of preparing for analysis a matrix containing bioparticles, comprising:
    drawing or dispensing a volume of the matrix along a flow path defined by a sampling body through a bed of porous polymer monolith in the flow path, which bed is of sufficient length along the flow path whereby the bed adsorbs the bioparticles and a sub-volume of the matrix substantially free of the bioparticles remains adjacent to the bioparticles in the sampling body; and
    recovering matrix from the sub-volume for analysis.

2. A method according to claim 1 wherein said body is a tubular body and the bed is a plug of the porous polymer monolith that fills a cross-section of the flow path.

3. A method according to claim 2 wherein the porous polymer monolith is a result of polymerisation of two or more monomers in the presence of two or more porogens.

4. A method according to claim 1 including forming the bed in situ by initiation of a polymerisation mixture within said body.

5. A method according to claim 4 wherein said initiation is by ultraviolet radiation.

6. A method according to claim 1 wherein the porous polymer monolith is a result of polymerisation of two or more monomers in the presence of two or more porogens.

7. A method according to claim 6 wherein the monomers are methacrylates and the porogens include an alcohol and an alkane.

8. A method according to claim 1 wherein the porous monomer monolith is selected to adsorb at least red blood cells from whole or buffered blood.

9. A method according to claim 8 wherein the porous polymer monolith is selected to additionally adsorb white blood cells and platelets from the whole or buffered blood whereby to obtain a cell-free plasma or plasma-like fraction.

* * * * *